United States Patent [19]

Graham et al.

[11] Patent Number: 5,342,899
[45] Date of Patent: Aug. 30, 1994

[54] PROCESS FOR RECYCLING AQUEOUS FLUID ABSORBENTS FINES TO A POLYMERIZER

[75] Inventors: Andrew T. Graham, Midland, Mich.; Herbert Gartner, Baden Baden, Fed. Rep. of Germany

[73] Assignee: The Dow Chemical Company, Midland, Mich.

[21] Appl. No.: 701,232

[22] Filed: May 16, 1991

[51] Int. Cl.$^5$ .................. C08F 265/02; C08F 267/02
[52] U.S. Cl. .................... 525/301; 125/296; 125/305; 125/309; 125/293; 525/274; 264/37; 521/405
[58] Field of Search .............. 525/37, 296, 305, 309, 525/293, 274, 301, ; 521/40.5; 264/37

[56] References Cited

U.S. PATENT DOCUMENTS

| | | |
|---|---|---|
| 4,727,097 | 2/1988 | Kobayashi et al. . |
| 4,914,066 | 4/1990 | Woodrum . |
| 4,950,692 | 8/1990 | Lewis et al. . |
| 4,970,267 | 11/1990 | Bailey et al. . |
| 4,985,467 | 1/1991 | Kelly et al. . |
| 4,990,541 | 2/1991 | Nielsen et al. . |
| 5,011,864 | 4/1991 | Nielsen et al. . |
| 5,064,582 | 11/1991 | Sutton et al. ............... 528/499 |

FOREIGN PATENT DOCUMENTS

| | | |
|---|---|---|
| 0425269 | 5/1991 | European Pat. Off. . |
| 0437816 | 7/1991 | European Pat. Off. . |
| 0454497 | 10/1991 | European Pat. Off. . |
| 0463388 | 1/1992 | European Pat. Off. . |
| 4021847 | 1/1992 | Fed. Rep. of Germany . |
| 9008789 | 8/1990 | PCT Int'l Appl. . |
| 9201008 | 1/1992 | PCT Int'l Appl. . |

*Primary Examiner*—John Kight, III
*Assistant Examiner*—Duc Truong

[57] ABSTRACT

A process is described for recycling dry aqueous fluid absorbent polymer fines into a process that includes a polymerization step for making the aqueous fluid absorbent polymer. The process requires recovering the dry polymer fines, mixing the fines with a polymerizable monomer solution for making the aqueous fluid absorbent polymer and polymerizing the mixture of fines and monomer to form the aqueous fluid absorbent polymer. In the process the fines are incorporated into the new polymer gel and becomes indistinguishable therefrom. The gel may then comminuted into a particulate dried and then separated into a portion having a desired minimum particle size in a fines portion having less than the desired size. The fines portion is then recycled up to about 30 percent by weight based on gel solids may be recycled for the preferred polyacrylate based aqueous fluid absorbent polymer.

12 Claims, No Drawings

PROCESS FOR RECYCLING AQUEOUS FLUID ABSORBENTS FINES TO A POLYMERIZER

BACKGROUND OF THE INVENTION

The invention relates to recycling dry fines that are generally difficult to hydrate into a main product stream. More particularly, the invention relates to reprocessing fines generated in the production of fluid absorbent polymers and copolymers.

Water-swellable polymers and copolymers are well known for their use as absorbents for aqueous fluids in diapers, sanitary products and the like. Certain of these polymers, for example those prepared from monomers of acrylic acid or methacrylie acid or their respective alkali metal or ammonium salts and typically lightly crosslinked with a crosslinking monomer having at least two polymerizable double bonds, exhibit exceptionally high capacity for adsorbing liquids and are further characterized as having good physical integrity in processing and use.

These water swellable polymers/copolymers are often employed in a particulate form of a desired particle size that effectively promotes contact with the fluid to be absorbed. In the production of acrylic acid-based copolymers by the gel formation method, a significant portion of "fines" material, that particulate material less than about 75 mesh (200 micrometers), is typically generated from the process of manufacturing the absorbent product. These processes generally include, after the gel polymer or copolymer gel is formed, a number of drying, gel breakup and grinding unit operations until an optional amount of product of a final acceptable particle size range is achieved. In the course of the process, 8–11 percent by weight of the final product may be fines, that is, particulate polymer that is finer than the desired minimum size suitable for the intended end-use of the polymer.

Initially, users employed the entire dry product, including fines, in their absorbent products. It was soon discovered, however, that the inclusion of fines resulted in lower product performance. One difficulty that often occurs when fine particles are initially contacted with an aqueous fluid is a "gel blocking" phenomenon. Upon initial hydration of a tightly packed mass of fines, only the outside layer is wetted because the fines form such a dense polymeric network that neither capillary action nor diffusion will permit penetration of the fluid into uniform contact with the interior particles. The result is a substantially reduced overall capacity of the absorbent polymer to absorb and hold aqueous fluids. In addition, for some products such as diapers, the fines material may sift from the product.

An initial solution to the fines problem was simply to screen the fines from the product. The resulting fines were stored as off-specification product with the intention of recycling the fines into the process or reprocessing them into larger sized particles through agglomeration. However, attempts at recycling the fines into the process have heretofor proved generally unsuccessful, requiring significant additional processing steps and equipment. A major difficulty with the fines particles is that they are extremely difficult to rewet for uniform blending into the main product stream.

In U.S. Pat. No. 4,950,692 superabsorbent polyacrylate fines are rehydrated to gel form by agitating for relatively long periods of time, typically one-half to one hour, followed by blending with the main gel product stream or drying and then blending with the dry product. In U.S. patent application Ser. No. 07/407,840, fines are rehydrated by rewetting under high shear conditions. While residence times for rewetting the fines are greatly reduced over U.S. '692, the recycling process does require the introduction of relatively high performance equipment into the process.

A number of workers have attempted to agglomerate fines to produce a larger size particulate for reintroduction into the product stream. These agglomeration techniques generally involved treating the fines with water or other binding agent in an environment such as a fluidized bed. The difficulty with this approach is that these processes fail to produce a product that is sufficiently bound together to survive forming into finished products without attriting and recreating the objectionable fine material, either in the process for making the aqueous fluid absorbents or in the customer's plant or product.

Thus, in view of the difficulties of the prior efforts to recycle aqueous fluid absorbent polymer fines, it would be desirable to provide a process that recycles fines into a main product stream of polymer/copolymer such that the finished product absorbent capacity and particulate integrity are equivalent to the material normally produced of a desired particle size. Such a process should not add significant processing steps or processing time.

SUMMARY OF THE INVENTION

The process of the invention is directed to recycling dry aqueous fluid absorbent polymer fines, generally polymer less than a desired size, into a process including a polymerization step for making said super absorbent polymer. The recycled fines are generally less than about 75 mesh (200 micrometers). The process comprises: P1 recovering dry polymer fines from said aqueous fluid absorbent polymer;

mixing said fines with a polymerizable monomer solution for making said aqueous fluid absorbent polymer; and polymerizing said mixture of fines and monomer to form said aqueous fluid absorbent polymer.

Generally, the process preferably further comprises:

comminuting the aqueous fluid absorbent polymer from said polymerizing step;

drying said comminuted polymer;

separating said dried polymer particulate into a portion having a desired minimum particle size and a fines portion having less than said desired size; and recycling said fines portion to the polymerizing step for forming said aqueous fluid absorbent polymer.

The preferred aqueous fluid absorbent polymer of interest, that is, the monomer solution from which it is made, includes water-soluble ethylenically unsaturated monomer mixtures or salts thereof, preferably an amide, carboxylic acid or its esters, vinyl amines or their salts or mixtures thereof.

Most preferably said polymer is a crosslinked polymer of polyacrylic acid, sodium polyacrylate or copolymers thereof crosslinked with a polyvinyl monomer.

Said monomer solution may include a monomer capable of graft polymerizing with at least one other component of said monomer mixture.

The aqueous fluid absorbent material of the invention is preferably a water-swellable fluid absorbent gel, that is, a partially neutralized copolymer that is lightly crosslinked, preferably of acrylic acid, methacrylic acid, crotonic acid or isocrotonic acid.

The amount of fines mixed into said monomer solution is limited to that amount which does not adversely affect the desired aqueous fluid absorbent characteristics of said polymer. An advantage of the process of the invention is that a relatively large amount of fines may be recycled or reprocessed without significantly adversely affecting the aqueous fluid absorbent characteristics desired in the polymer product. The amount that may be recycled generally is substantially in excess of the 8–11 weight percent typically generated in the gel process and may range, if required, up to 30 weight percent, based upon the solids content of the polymer gel of the invention. Preferably the fines recycled portion comprises 5–15 percent based upon the solids content of the gel.

DETAILED DESCRIPTION OF THE INVENTION

In the production and handling of solid aqueous fluid absorbent polymers to produce a particulate product having a desirable particle size, for example suitable for incorporation in personal care articles such as diapers, drying and grinding portions of the typical gel process naturally create a fines fraction of particles that are undesirably small for the intended uses. This particle size fraction, hereinafter referred to as "fines", in addition to being undesirably small for the intended use is often small enough to create dusting problems in production. Such dusty fines may create materials handling problems in the process as well as represent a risk of becoming airborne in a manufacturing facility. In the products in which employed, the fines material is often a source of performance difficulties because of its well-known tendency to gel block upon initial wetting. In addition, there may also be difficulty in containing the fines in the product.

The present invention is a process by which a fines portion of an aqueous fluid absorbent polymer, created by natural attrition during its manufacture or incorporation into a useful article, is recycled into the polymerization reaction which originally created the aqueous fluid polymer. By means of this process, what has often been in the past an accepted yield loss in manufacturing and handling such materials is now minimized or eliminated. The result is a product aqueous fluid absorbent particulate that remains unitary in nature even under the stresses imposed by hydration, as can easily be seen by observation of the hydration process under low power microscope.

The water-swellable or lightly crosslinked hydrophilic polymers or copolymers that are of particular interest in the fines recycling process of the present invention are any of those capable of adsorbing large quantities of aqueous fluids. Examples of such polymers and methods for making them are found in U.S. Pat. Nos. 3,997,484; 3,926,891; 3,935,099; 4,090,013; and 4,190,562, the relevant parts of which are herein incorporated by reference. In general, such polymers are prepared from water-soluble $\alpha, \beta$-ethylenically unsaturated monomers such as mono and polycarboxylic acids, acrylamide or their derivatives. Examples of suitable mono-carboxylic acids include acrylic acid, methacrylic acid, crotonic acid and isocrotonic acid and their alkali metal and ammonium salts, as well as sulfoethyl methacrylate and its sodium salt or 2-acrylamido-2-methylpropane sulfonic acid or its sodium salt. Suitable polycarboxylic acids include maleic acid, fumaric acid and itaconic acid. Suitable acrylamide derivatives include methylacrylamide and N,N-dimethylacrylamide. The preferred monomers include acrylic acid and methacrylic acid and their respective alkali metal or ammonium salts. The polymers may be modified, for example by inclusion of graftable moieties in the monomer solutions.

Organic compounds having two or more ethylenic groups copolymerizable with the water-soluble monomers can be used as crosslinking monomers. Exemplary multifunctional crosslinking monomers include diacrylate or dimethacrylate esters of ethylene glycol, diethylene glycol, triethylene glycol, polyethylene glycol, 1,4-butane diol and the like, as noted in U.S. Pat. No. 4,286,082. Others are methylene bisacrylamide, di- and tri-allylamines and allyl [meth]acrylate esters. The degree of crosslinking is selected such that water absorption capacity of the polymer is not reduced or so low that the absorbent becomes sticky on contact with fluid and exhibits a low initial absorption rate.

The preferred aqueous fluid absorbent particulate is derived from a monomer solution comprising polyacrylic acid. In the most preferred solution, the polyacrylic acid is at least partially neutralized and partially crosslinked salt. The monomer mixture solution may include graft polymerizable moieties such as starch, polyvinyl alcohol and the like, as well as other monomers that copolymerize with polyacrylic acid or its salt. In the process, the acrylic acid is preferably neutralized with an alkali base such as a sodium, ammonium, potassium hydroxide or carbonates.

In the partially neutralized, partially crosslinked polyacrylic acid monomer system, the acrylic acid concentration in the polymerization phase will range from about 10 to 40 weight percent based upon the solids concentration of the gel in the reactor. Preferably, the acrylic acid concentration in the monomer solution is about 20 to 40 percent and most preferably 25 to 35 percent. The acrylic acid component will generally be about 30 to 100 percent neutralized, preferably 40 to 80 percent, most preferably 55 to 75 percent. In general, a crosslinker, if utilized, will range from 0.001 to 5 percent, based upon the weight of solids in the reactor with a preferred range of 0.2 to 1 percent. The polymer fines that may be recycled to the process may comprise up to at least about 30 percent by weight based upon the solids in the reactor. A preferred operating range is 5 to 15 percent by weight, in order to minimize impact upon aqueous fluid absorbent performance qualities of the product.

The method and apparatus for making the gel polymerization product is entirely conventional, except for recycling the fines to the monomer solution prior to the polymerization step. The equipment utilized is also conventional with the principal reaction vessel typically a simple vertically agitated vessel or a horizontal single screw cylindrical mixer as described in U.S. Pat. No. 4,769,427 and EP 0 238 050. Other reactor vessels known in the art are suitable and other reaction devices such as a twin screw extruder described in U.S. Pat. No. 4,625,001 or a belt polymerizer described in U.S. Pat. No. 4,851,610 may be utilized.

In the polymerization step all well-known free radical initiation systems maybe utilized, including initiation systems based entirely on thermal initiators, as well as the many different combinations of redox initiation systems. The amounts of initiator employed are those chosen based on the needs the particular polymerization equipment and conditions of temperature and pressure at which it is desired to operate that equipment and are not otherwise constrained.

Generally, the water-soluble monomer and crosslinking monomer are polymerized in the presence of a polymerization initiator in any known manner such that a gel-like reaction product results. The gel polymer is dried, preferably by hot air at about 50° to 200° C. such that the moisture content of the polymer gel is between about 0.01 and 15 percent based on the total weight of the dried absorbent polymer. The dried polymer is then comminuted into a particulate product having a desired size particulates.

The following examples illustrate the products and process of the invention and are not intended to limit the invention only to their scope.

EXAMPLES 1, 2 and COMPARATIVE EXAMPLE A

Acrylic acid is charged to a one-liter reaction kettle provided with agitation followed by addition of trimethylolpropane triacrylate (TMPTA) crosslinking agent which after several minutes of stirring dissolves in the acrylic acid. To this solution is added Versenex® 80 chelating agent (40 percent aqueous solution of pentasodium salt of diethylene triamine pentacedic acid available from The Dow Chemical Company) and Airvol® 205, a low viscosity polyvinyl alcohol that is 87–89 percent hydrolyzed and has a 4 percent solution viscosity of 5–6 cp at 20° C. and is manufactured by Air Products Co. of Allentown, Pa., for stabilizing the TMPTA in aqueous medium. The monomer solution is then partially neutralized to about 65 percent of neutrality, with a sodium carbonate solution. The rate of addition of the alkali material is adjusted to accommodate $CO_2$ evolution.

In accord with the invention, polymer fines are added to the neutralized monomer mix with agitation. Again, the rate of agitation is controlled to avoid excess foaming of the $CO_2$ supersaturated monomer mixture. No fines are added for Comparative Example A.

The reactor contents are deoxygenated for 60 minutes and the initiator components are introduced. Polymerization is initiated and the temperature is allowed to rise to an initial desired level. The reactor is then maintained at a desired hold temperature for a period of time necessary for high monomer conversion to be achieved. In cases where higher levels of fines are added to the polymerization, the total heat release was reduced compared to the Comparative Example A polymerization. To insure similar temperature profiles for all polymerizations, a heated bath was employed to eliminate any differences derivable from differences in heat history.

The reaction is allowed to proceed until complete as evidenced by conversion of the monomers to polymer. After conversion is complete, the gel is removed from the reactor in small pieces that are then spread onto a nylon screen and dried in an oven at about 100° C. for about 16 hours. After drying, the polymer is cooled to room temperature and is pulverized to the desired particle size.

After the polymer is dried and ground to final particulate size, it is analyzed for residual acrylic acid, extractable centrifuge capacity, shear modulus, and absorption under load.

The above-process was repeated varying the amount of polymer fines introduced into the monomer solution between about zero and about 16.7 weight percent fines, based on the solids remaining in the finished, dried polymer. The ingredients employed in the process are shown in Table I below.

TABLE I

| Polymerization Ingredients (g) | Example 1 (8.3% Fines) | Example 2 (16.7% Fines) | Comparative Example A |
|---|---|---|---|
| Acrylic Acid | 273 | 250 | 300 |
| TMPTA | 1.91 | 1.75 | 2.1 |
| Versenex V-80 | 1.82 | 1.67 | 2.0 |
| Airvol 205, 5% | 1.36 | 1.25 | 1.5 |
| $Na_2CO_3$ | 131 | 120 | 144 |
| Water | 801 | 801 | 801 |
| Fines | 30 | 60 | None |
| INITIATORS | | | |
| $H_2O_2$ (30%) | 1.0 | 1.0 | 1.0 |
| $Na_2S_2O_8$ (10%) | 5.0 | 5.0 | 5.0 |
| Na erythorbate (10%) | 0.6 | 0.6 | 0.6 |

The fines employed in the examples are screened from conventional production DRYTECH® polymer which is a partially neutralized, partially crosslinked aqueous fluid absorbent polymer based on acrylic acid manufactured by The Dow Chemical Company in accord with Comparative Example A as described in U.S. Pat. No. 4,833,222, the relevant portions of which are incorporated by reference. The DRYTECH® polymer fines material employed is less than about 140 mesh (110 micrometers) and is derived from production material having an average 30 minute centrifuge capacity of 30.5 g/g, a 4-hour aqueous extractables of 7.2 percent and a residual acrylic acid monomer of 470 ppm.

Characteristics of the qualities of the dry particulate aqueous fluid absorbent polymer, for each level of fines addition to the polymerization step, are reported in Table II for polymerization hold temperatures of 80° and 50° C.

TABLE II

| Example | Centrifuged Capacities 30 min. [g/g] | | AUL [g/g] | | % Extractables | | Residual acrylic acid [ppm] | | Modulus [dynes/cm$^2$] | |
|---|---|---|---|---|---|---|---|---|---|---|
| | 50° C. | 80° C. | 50° C. | 80° C. | 50° C. | 80° C. | 50° C. | 80° C. | 50° C. | 80° C. |
| Example 1 | 25.7 | 28.2 | — | 24.7 | 2.5 | 7.3 | 1710 | 807 | 40,400 | 35,800 |
| Example 2 | 24.5 | 27.9 | — | 24.1 | 2.4 | 9.3 | 4087 | 718 | 40,300 | 31,700 |
| Comparative | 28.4 | 29.9 | — | 25.1 | 2.4 | 7.4 | 3533 | 816 | 35,900 | 30,100 |

TABLE II-continued

| Example | Centrifuged Capacities 30 min. [g/g] | | AUL [g/g] | | % Extractables | | Residual acrylic acid [ppm] | | Modulus [dynes/cm²] | |
|---|---|---|---|---|---|---|---|---|---|---|
| | 50° C. | 80° C. | 50° C. | 80° C. | 50° C. | 80° C. | 50° C. | 80° C. | 50° C. | 80° C. |
| Example A | | | | | | | | | | |

[1] The procedure for determining Centrifuged Capacity is described in EP 0 349 241, the relevant portions of which are incorporated by reference.
[2] The procedure for determining Absorbency Under Load (AUL) is described in EP 0 339 461, the relevant portions of which are incorporated by reference.
[3] The procedures for determining Percent Extractables and Residual Acrylic Acid are determined by dispensing 2 g of 80/100 mesh screen cut of polymer in 370 ml of 0.9 percent saline solution, shaking for 4 hours and filtering. The filtrate is then subjected to liquid chromatography to determine Residual Acrylic Acid and filtrated for acid content to determine percent extractables.
[4] The procedure for determining Modulus is described in RE 32,649, relevant portions of which are incorporated by reference.

Table II shows the effect of added fines on 30 minute centrifuge capacity of the polymerization product. The centrifuge capacity decreases with added fines.

EXAMPLE 3

A series of polymerizations identical to those of Examples 1 and 2 are performed for fines levels of 8.3 and 16.7 percent except that the amount of TMPTA crosslinker agent was varied. Table III reports the affect of crosslinker variation on centrifuge capacity for the two fines contents.

The absorbency under load (AUL) test measures the way in which polymer swells under pressure. Where recycled rehydrated fines have been added to the gel, by the method of the prior art, a decrease in AUL with increased fines addition level was experienced. Adding fines to the monomer prior to polymerization in accord with the present invention achieves satisfactory AUL without a substantial reduction in AUL. While there is some reduction at higher crosslinker levels, the degree of reduction is acceptable in view of the overall characteristics of the dry product achieved.

TABLE III

| Amount of TMPTA (%) | Hold Temperature (°C.) | Centrifuged Capacities 30 min. [g/g] | | % Extractables [%] | | AUL [g/g] | | Modulus [dynes/cm²] | |
|---|---|---|---|---|---|---|---|---|---|
| | | 8.3% fines | 16.7% Fines | 8.3% fines | 16.7% Fines | 8.3% fines | 16.7% Fines | 8.3% fines | 16.7% Fines |
| 0.7 | 80 | 28.2 | 27.9 | 7.3 | 9.2 | 24.7 | 24.1 | 34,100 | 31,700 |
| 0.5 | 80 | 29.9 | 28.6 | 10.6 | 11.8 | 22.6 | 23.8 | 24,000 | 28,400 |
| 0.3 | 80 | 32.8 | 30.4 | 13.1 | 12.9 | 21.3 | 20.4 | 21,200 | 24,300 |
| 0.7 | 50 | — | 28.6 | — | 3.2 | — | 27.8 | — | 36,600 |
| 0.5 | 50 | — | 27.6 | — | 5.8 | — | 24.8 | — | 35,600 |
| 0.3 | 50 | — | 27.5 | — | 6.1 | — | 26.1 | — | 35,700 |

Table III of Example 3 shows the response of centrifuge capacities to changes in TMPTA level for two levels of fine addition. A significant reduction from 0.7 percent TMPTA to to 0.3 percent TMPTA at 16.6 percent fines at an 80° C. whole temperature was required to bring the 30 minute centrifuge capacity back up to the zero fines level. A larger reduction in TMPTA level would have been required at lower whole temperatures.

EXAMPLES 4–6

Sodium acrylate aqueous fluids absorbent polymer is made utilizing a 200 liter reactor, employing a scaled-up version of the lab recipe noted above, at a higher solids content. Fines added to the monomer are at about a 7, 15 and 20 percent, based upon the solids content of the gel product. Table IV reports the results of these examples, which are consistent with those presented above wherein the centrifuged capacity decreases with increasing recycled fines levels with all other properties remaining in the normal and acceptable range.

TABLE IV

| Examples | Example 4 | Example 5 | Example 6 |
|---|---|---|---|
| Fines, % | 7 | 15 | 20 |
| Cent cap, (30 min) g/g | 29.4 | 26.8 | 25.1 |
| AUL, g/g | 26 | 23 | 24 |
| 16 hr ext, % | 5.6 | 4.7 | 4.5 |
| Residual AA, ppm | 416 | 800 | 251 |

EXAMPLE 7 AND COMPARATIVE EXAMPLES B AND C

Test Procedure

A beaker containing 40 ml of saline solution is vigorously stirred on a magnetic mixer. Two grams of an aqueous fluid absorbent polymer are added and the time is recorded for the disappearance of the vortex caused by the magnetic stirrer. A second 10 ml portion of saline solution, this portion containing a blue dye, is added and absorbency observed.

Examples Tested

An aqueous fluid absorbent product comprising (1) agglomerated fines and designated as Comparative Example B; (2) a product produced by blending a hydrated fines particulate with gel and designated as Comparative Example C; and (3) the product of the present invention requiring recycling fines to the polymerization process and designated as Example 7 are tested as indicated above.

Comparative Example B is made by mixing fines with water at high speed, drying and screening to produce a 20 to 100 mesh particulate. Comparative Example C is made by the process of hydrating fines at high shear in accord with U.S. patent application Ser. No. 07/407,840.

Results

For materials made by Comparative Examples B and C of the prior art, the blue dye penetrated only about ¼ of volume of the original swollen gel. In the test for Example 7, the product of the process of this invention, the blue color was present throughout the volume of the beaker.

The non-uniformity of the blue color for the first test indicates gel blocking as the particles come apart during hydration. The breaking-up of product into small pieces upon hydration is observable under a low power microscope. The uniform blue color appearing with the product of the invention indicates that no gel blocking has occurred and that the product retains its unitary nature even under the stresses imposed by hydration.

What is claimed is:

1. A process for recycling dry aqueous fluid absorbent polymer fines into a process that includes a polymerization step for making said aqueous fluid absorbent polymers, comprising:
   recovering dry polymer fines from said aqueous fluid absorbent polymer;
   mixing said fines with a polymerizable monomer solution for making said aqueous fluid absorbent polymer; and
   polymerizing said mixture of fines and monomer to form said aqueous fluid absorbent polymer.

2. The process of claim 1, further comprising:
   comminuting the aqueous fluid absorbent polymer from said polymerizing step;
   drying said comminuted polymer;
   separating said dried polymer particulate into a portion having a desired minimum particle size and a fines portion having less than said desired size; and
   recycling said fines portion to the polymerizing step for forming said aqueous fluid absorbent polymer.

3. The process of claim 1 wherein said monomer solution includes water-soluble ethylenically unsaturated monomer mixtures or salts thereof.

4. The process of claim 3 wherein said ethylenically unsaturated monomer is an amide, carboxylic acid or its esters, vinyl amines or their salts or mixtures thereof.

5. The process of claim 1 wherein said polymer is a crosslinked polymer of polyacrylic acid, sodium polyacrylate or copolymers thereof, crosslinked with a polyvinyl monomer.

6. The process of claim 4 wherein said monomer solution includes a monomer capable of graft polymerizing with at least one other component of said monomer solution.

7. The process of claim 4 wherein said monomer solution includes an initiator.

8. The process of claim 1 wherein said polymerizing step produces a water-swellable, aqueous fluid absorbent polymer or copolymer gel.

9. The process of claim 1 wherein said polymer fines are less than 75 mesh (200 micrometers).

10. In a process for making an aqueous fluid absorbent polymer of the type wherein the monomer solution is polymerized to form a gel polymer, said gel is comminuted, dried and classified to separate a particulate product of a desired size from particulate fines, the improvement, for recycling said fines and any such fines from other product handling, said process, comprising:
    mixing said fines with a monomer solution that is polymerizable to form said aqueous fluid absorbent polymer; and
    polymerizing said mixture of fines and monomer to form a gel product for further processing into a dried particulate product of desired particle size,
    wherein the amount of fines mixed into said monomer solution is limited to that amount which is does not adversely affect the desired aqueous fluid absorbent characteristics desired of said polymer.

11. The process of claim 10 wherein said polymer is a partially crosslinked water-swellable copolymer of acrylic acid and to alkali salts.

12. The process of claim 11 wherein the recycled fines comprises up to about 30 weight percent, based upon the solids content of the polymerized aqueous fluid absorbent gel.

* * * * *